(12) United States Patent
Parrish

(10) Patent No.: US 9,725,437 B2
(45) Date of Patent: Aug. 8, 2017

(54) FATTY ACID SYNTHASE INHIBITORS

(71) Applicant: GlaxoSmithKline Intellectual Property (No.2) Limited, Brentford, Middlesex (GB)

(72) Inventor: Cynthia Ann Parrish, Collegeville, PA (US)

(73) Assignee: GLAXOSMITHKLINE INTELLECTUAL PROPERTY (NO.2) LIMITED, Brentford, Middlesex (GB)

(*) Notice: Subject to any disclaimer, the term of this patent is extended or adjusted under 35 U.S.C. 154(b) by 0 days.

(21) Appl. No.: 15/259,363

(22) Filed: Sep. 8, 2016

(65) Prior Publication Data

US 2016/0376257 A1    Dec. 29, 2016

Related U.S. Application Data

(63) Continuation of application No. 14/655,185, filed as application No. PCT/IB2014/058174 on Jan. 10, 2014, now abandoned.

(60) Provisional application No. 61/750,872, filed on Jan. 10, 2013.

(51) Int. Cl.
*C07D 401/14* (2006.01)
*A61K 31/4709* (2006.01)
*A61K 45/06* (2006.01)

(52) U.S. Cl.
CPC ........ *C07D 401/14* (2013.01); *A61K 31/4709* (2013.01); *A61K 45/06* (2013.01)

(58) Field of Classification Search
CPC ... C07D 401/14; A61K 45/06; A61K 31/4709
See application file for complete search history.

(56) References Cited

FOREIGN PATENT DOCUMENTS

| WO | 2011/103546 | * | 8/2011 |
| WO | WO 2011/103546 A1 | | 8/2011 |
| WO | WO2012/064642 | | 5/2012 |
| WO | WO2013/028447 | | 2/2013 |

OTHER PUBLICATIONS

Asturias, et al., *Nature Struct. Mol. Biol.*, 12:225-232 (2005).
Davis, et al., *Journal of Pharmaceutical Sciences*, 98:362-377 (2009).
Kuhajda, FP, *Nutrition*, 16:202-208 (2000).
Maier, et al., *Science*, 311:1258-1262 (2006).
Medes, et al., *Cancer Research*, 13:27-29 (1953).
Menendez, et al., *Nature Reviews Cancer*, 7:763-777 (2007).
Wakil, SJ, *Lipids*, 39:1045-1053 (2004).
Weiss, et al., *Biological Chemistry-Hoppe-Seyler*, 367(9):905-912 (1986).
Xiang, et al., *Journal of Pharmaceutical Sciences*, 95:2657-2672 (2006).

* cited by examiner

*Primary Examiner* — D M Seaman
(74) *Attorney, Agent, or Firm* — Wayne J. Dustman; Edward R. Gimmi

(57) ABSTRACT

This invention relates to triazolones and triazolones for the modulation, notably the inhibition of the activity or function of fatty acid synthase (FAS). Suitably, the present invention relates to the use of triazolones in the treatment of cancer.

10 Claims, No Drawings

FATTY ACID SYNTHASE INHIBITORS

This application is a Continuation of U.S. application Ser. No. 14/655,185 filed Jun. 24, 2015, which is a 371 of International Application No. PCT/IB2014/058174 filed Jan. 10, 2014, which claims priority to U.S. Provisional Application No. 61/750,872 filed Jan. 10, 2013, which are incorporated herein in their entirety.

FIELD OF INVENTION

This invention relates to novel triazolones which are inhibitors of fatty acid synthase (FAS), to pharmaceutical compositions containing them, to processes for their preparation, and to their use in therapy for the treatment of cancers.

BACKGROUND

Fatty acids have an essential role in a variety of cellular processes including building blocks for membranes, anchors for targeting membrane proteins, precursors in the synthesis of lipid second messengers and as a medium to store energy, (Menendez J S and Lupu R, *Fatty acid synthase and the lipogenic phenotype in cancer pathogenesis*, Nature Reviews Cancer, 7: 763-777 (2007)). Fatty acids can either be obtained from the diet or can be synthesized de novo from carbohydrate precursors. The biosynthesis of the latter is catalyzed by the multi-functional homodimeric FAS. FAS synthesizes long chain fatty acids by using acetyl-CoA as a primer and Malonyl Co-A as a 2 carbon donor, and NADPH as reducing equivalents (Wakil S J, *Lipids, Structure and function of animal fatty acid synthase*, 39: 1045-1053 (2004), Asturias F J et al., *Structure and molecular organization of mammalian fatty acid synthase*, Nature Struct. Mol. Biol. 12:225-232 (2005), Maier T, et al., *Architecture of Mammalian Fatty Acid Synthase at 4.5 Å Resolution*, Science 311:1258-1262 (2006)).

De novo fatty acid synthesis is active during embryogenesis and in fetal lungs where fatty acids are used for the production of lung surfactant. In adults, most normal human tissues preferentially acquire fatty acids from the diet. Therefore, the level of de novo lipogenesis and expression of lipogenic enzymes is low (Weiss L, et al., *Fatty-acid biosynthesis in man, a pathway of minor importance. Purification, optimal assay conditions, and organ distribution of fatty-acid synthase. Biological Chemistry Hoppe-Seyler*367 (9):905-912 (1986)). In contrast, many tumors have high rates of de novo fatty acid synthesis (Medes G, et al., *Metabolism of Neoplastic Tissue. IV. A Study of Lipid Synthesis in Neoplastic Tissue Slices in Vitro*, Can Res, 13:27-29, (1953)). FAS has now been shown to be overexpressed in numerous cancer types including prostate, ovary, colon, endometrium, lung, bladder, stomach and kidney (Kuhajda F P, *Fatty-acid synthase and human cancer: new perspectives on its role in tumor biology*, Nutrition; 16:202-208 (2000)). This differential expression and function of FAS in tumors and normal cells provide an approach for cancer therapy with the potential of a substantial therapeutic window.

Pharmacological and small interference RNA mediated inhibition of FAS has demonstrated a preferential inhibition of cancer cell proliferation. Additionally, these inhibitors induce apoptosis in cancer cells in vitro and retard growth in human tumors in murine xenograft models in vivo (Menendez J S and Lupu R, Nature Reviews Cancer, 7: 763-777 (2007)). Based upon these findings, FAS is considered a major potential target of anti-neoplastic intervention.

SUMMARY OF THE INVENTION

This invention relates to compounds or pharmaceutically acceptable salt thereof selected from the group consisting of:
(S)-3-((1-(cyclopropanecarbonyl) pyrrolidin-3-yl)methyl)-4-(2-fluoro-4-(3-methylquinolin-7-yl)phenyl)-1H-1,2,4-triazol-5(4H)-one;
(S)-4-(4-(3-chloroquinolin-7-yl)-2-fluorophenyl)-3-((1-(cyclopropanecarbonyl)pyrrolidin-3-yl)methyl)-1H-1,2,4-triazol-5(4H)-one;
(S)-3-((1-(cyclopropanecarbonyl)pyrrolidin-3-yl)methyl)-4-(2-fluoro-4-(3-fluoroquinolin-7-yl)phenyl)-1H-1,2,4-triazol-5(4H)-one;
(S)-4-(2-fluoro-4-(3-fluoroquinolin-7-yl)phenyl)-3-((1-propionylpyrrolidin-3-yl)methyl)-1 H-1,2,4-triazol-5(4H)-one;
(S)-4-(2-fluoro-4-(3-methylquinolin-7-yl)phenyl)-3-((1-propionylpyrrolidin-3-yl)methyl)-1 H-1,2,4-triazol-5(4H)-one;
(S)-4-(4-(3-chloroquinolin-7-yl)-2-fluorophenyl)-3-((1-propionylpyrrolidin-3-yl)methyl)-1 H-1,2,4-triazol-5(4H)-one;
(S)-4-(2-fluoro-4-(3-methylquinolin-7-yl)phenyl)-1-methyl-3-((1-propionylpyrrolidin-3-yl)methyl)-1H-1,2,4-triazol-5(4H)-one;
(S)-4-(4-(3-chloroquinolin-7-yl)-2-fluorophenyl)-1-methyl-3-((1-propionylpyrrolidin-3-yl)methyl)-1H-1,2,4-triazol-5(4H)-one;
(S)-4-(4-(3-chloroquinolin-7-yl)-2-fluorophenyl)-3-((1-(cyclopropanecarbonyl)pyrrolidin-3-yl)methyl)-1-methyl-1H-1,2,4-triazol-5(4H)-one; and
(S)-4-(2-fluoro-4-(3-fluoroquinolin-7-yl)phenyl)-1-methyl-3-((1-propionylpyrrolidin-3-yl)methyl)-1H-1,2,4-triazol-5(4H)-one.

DETAILED DESCRIPTION OF THE INVENTION

This invention also relates to the compound (S)-4-(2-fluoro-4-(3-methylquinolin-7-yl)phenyl)-1-methyl-3-((1-propionylpyrrolidin-3-yl)methyl)-1H-1,2,4-triazol-5(4H)-one, having the Formula (I)

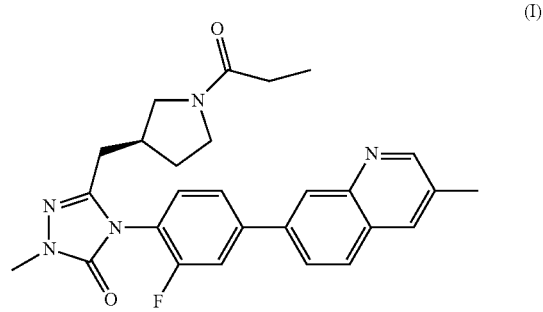

(I)

or a pharmaceutically acceptable salt thereof.

This invention also relates to the compound (S)-4-(4-(3-chloroquinolin-7-yl)-2-fluorophenyl)-1-methyl-3-((1-propionylpyrrolidin-3-yl)methyl)-1H-1,2,4-triazol-5(4H)-one having the Formula (II)

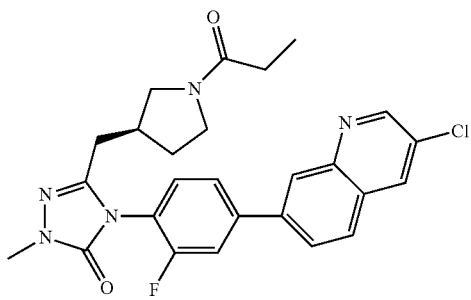

(II)

or a pharmaceutically acceptable salt thereof.

This invention also relates to the compound (S)-4-(4-(3-chloroquinolin-7-yl)-2-fluorophenyl)-3-((1-(cyclopropanecarbonyl)pyrrolidin-3-yl)methyl)-1-methyl-1H-1,2,4-triazol-5(4H)-one having the Formula (III)

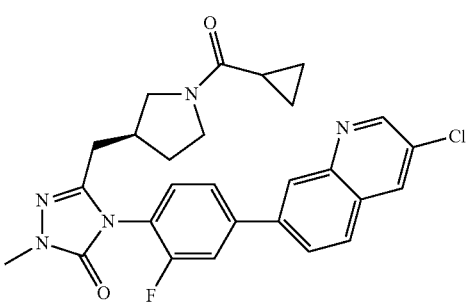

(III)

or a pharmaceutically acceptable salt thereof.

This invention also relates to the compound (S)-4-(4-(3-chloroquinolin-7-yl)-2-fluorophenyl)-3-((1-(cyclopropanecarbonyl)pyrrolidin-3-yl)methyl)-1H-1,2,4-triazol-5(4H)-one having the Formula (IV)

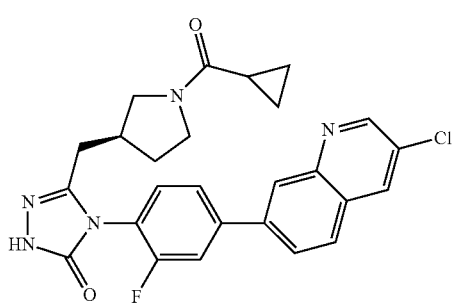

(IV)

or a pharmaceutically acceptable salt thereof.

In one embodiment of the invention the compound has an $IC_{50}$ for FAS inhibition of <20 nM versus human FAS. In another embodiment, the compound displays a low in vivo clearance. In another embodiment, the compound displays a clearance of less than about 17 mL/min/kg when administered intravenously to a rat. In yet another embodiment, the compound displays a clearance of less than about 30 mL/min/kg when administered intravenously to a mouse. In another embodiment, the compound is capable of achieving a DNAUC of at least about 101 ng·h/mL/mg/kg when administered orally to a mammal. In one aspect the mammal is a rodent.

As is understood in the art, various methods may be employed to collect, measure and assess pharmacokinetic data such as compound concentration in blood, plasma and/or other tissue. As is also understood in the art, various methods may be employed to collect, measure and assess various pharmacodynamic data such as, but not limited to, glucose levels, FAS activity, synthesis of fatty acid and other biomarker levels in blood and/or plasma and/or other tissue.

In another embodiment, the invention relates to a pharmaceutical composition comprising a compound pharmaceutically acceptable salt thereof according to any of the compounds of the invention.

In another embodiment, methods are provided for treating cancer in a human in need thereof comprising administering to said human a compound of the present invention or a pharmaceutically acceptable salt thereof. In one embodiment method are provided for treating cancer in a human in need thereof comprising administering to said human a pharmaceutical composition of the present invention. In one embodiment the cancer is selected from the group consisting of: gastric, brain (gliomas), glioblastomas, leukemias, lymphomas, breast, inflammatory breast cancer, Wilm's tumor, Ewing's sarcoma, Rhabdomyosarcoma, ependymoma, medulloblastoma, colon, head and neck, kidney, lung, liver, melanoma, renal, ovarian, pancreatic, prostate, sarcoma, osteosarcoma, bladder, stomach, and giant cell tumor of bone and thyroid.

In another embodiment, methods of treating cancer in a mammal in need thereof comprises: administering to such mammal a therapeutically effective amount of
    at least one compound of the invention or a pharmaceutically acceptable salt thereof; and
    at least one anti-neoplastic agent.

This invention also relates to compounds exemplified in the Experimental section. Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. In general, the salts are formed from pharmaceutically acceptable inorganic and organic acids. More specific examples of suitable acid salts include maleic, hydrochloric, hydrobromic, sulphuric, phosphoric, nitric, perchloric, fumic, fumaric, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthalene-2-sulfonic, benzenesulfonic, hydroxynaphthoic, hydroiodic, malic, teroic, tannic, and the like.

Other representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, oxalate, pamoate (embonate), palmitate, pantothenate, phosphate/diphosphate, polygalacturonate, salicylate, stearate, subacetate, succinate, sulfate, tannate, tartrate, teoclate, tosylate, triethiodide, and valerate salts.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compounds of the invention, including but not limited to, Formula (I), Formula (II), Formula (III), and/or Formula (IV) or a salt thereof may exist in stereoisomeric forms (e.g., it contains an asymmetric carbon atom). The individual stereoisomers (enantiomers) and mixtures of these are included within the scope of the present invention. The invention also covers the individual isomers of the compound or salt represented by compounds of the invention, including but not limited to, Formula (I), Formula (II), Formula (III), and/or Formula (IV) as mixtures with isomers thereof in which one or more chiral centers are inverted. Likewise, it is understood that a compound or salt of compounds of the invention may exist in tautomeric forms other than that shown in the formula and these are also included within the scope of the present invention. It is to be understood that the present invention includes all combinations and subsets of the particular groups defined herein above. The scope of the present invention includes mixtures of stereoisomers as well as purified enantiomers or enantiomerically/diastereomerically enriched mixtures. Also included within the scope of the invention are individual isomers of the compound represented by compounds of the invention as well as any wholly or partially equilibrated mixtures thereof. The present invention also includes the individual isomers of the compound or salt represented by compounds of the invention as well as mixtures with isomers thereof in which one or more chiral centers are inverted. It is to be understood that the present invention includes all combinations and subsets of the particular groups defined hereinabove.

The invention also includes various deuterated forms of the compounds of the invention. Each available hydrogen atom attached to a carbon atom may be independently replaced with a deuterium atom. A person of ordinary skill in the art will know how to synthesize deuterated forms of the compounds of the invention. Commercially available deuterated starting materials may be employed in the preparation of deuterated forms of the compounds of the invention, or they may be synthesized using conventional techniques employing deuterated reagents (e.g. lithium aluminum deuteride).

DEFINITIONS

Terms are used within their accepted meanings. The following definitions are meant to clarify, but not limit, the terms defined.

As used herein, the term "alkyl" refers to a straight or branched chain hydrocarbon radical, preferably having from one to twelve carbon atoms, which may be unsubstituted or substituted, saturated or unsaturated with multiple degrees of substitution included within the present invention. When optionally substituted, the alkyl group is unsubstituted or substituted with suitable substituents selected from the group consisting of halogen, amino, substituted amino, cyano, hydroxyl, alkoxy, alkylthio, alkylsulfonyl, aminosulfonyl, carboxylic acid, carboxylic ester, carboxamide, aminocarbonyl, and heterocyclyl. Examples of "alkyl" as used herein include, but are not limited to, methyl, ethyl, propyl, isopropyl, isobutyl, n-butyl, t-butyl, isopentyl, n-pentyl, and the like, as well as substituted versions thereof.

As used herein, the term "cycloalkyl" refers to an unsubstituted or substituted mono- or polycyclic non-aromatic saturated ring. Exemplary "cycloalkyl" groups include, but are not limited to, cyclopropyl, cyclobutyl, cyclopentyl, cyclohexyl, cycloheptyl, and the like, as well as unsubstituted and substituted versions thereof.

As used herein, the term "alkoxy" refers to the group —OR$^a$, where R$^a$ is $C_1$-$C_4$alkyl or $C_3$-$C_7$cycloalkyl as defined above. The term "$C_1$-$C_4$alkoxy" refers to a straight- or branched-chain hydrocarbon radical having at least 1 and up to 4 carbon atoms attached through an oxygen linking atom. Exemplary "($C_1$-$C_4$)alkoxy" groups useful in the present invention include, but are not limited to, methoxy, ethoxy, n-propoxy, isopropoxy, n-butoxy, s-butoxy, and t-butoxy.

"Heterocycloalkyl" represents a group or moiety comprising a non-aromatic, monovalent monocyclic or bicyclic radical, which is saturated or partially unsaturated, containing 3 to 10 ring atoms, which includes 1 to 3 heteroatoms independently selected from nitrogen, oxygen and sulfur. Illustrative examples of heterocycloalkyls useful in the present invention include, but are not limited to, azetidinyl, pyrrolidinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, morpholinyl, thiomorpholinyl, tetrahydropyranyl, dihydropyranyl, 1,3-dioxanyl, 1,4-dioxanyl, 1,3-oxathiolanyl, 1,3-oxathianyl, 1,3-dithianyl, hexahydro-1H-1,4-diazepinyl, azabicylo[3.2.1]octyl, azabicylo[3.3.1]nonyl, azabicylo[4.3.0]nonyl, oxabicylo[2.2.1]heptyl and 1,5,9-triazacyclododecyl.

As used herein, the term "heterocyclyl" refers to an unsubstituted or substituted mono- or polycyclic ring system containing one or more heteroatoms. Preferred heteroatoms include nitrogen, oxygen, and sulfur, including N-oxides, sulfur oxides, and dioxides. A heterocyclic ring may be, but is not limited to, three to eight-membered and is either fully saturated or has one or more degrees of unsaturation. Multiple degrees of substitution are included within the present definition. Examples of "heterocyclic" groups include, but are not limited to tetrahydrofuranyl, pyranyl, 1,4-dioxanyl, 1,3-dioxanyl, piperidinyl, pyrrolidinyl, morpholinyl, azetidinyl, piperazinyl, pyrrolidinonyl, piperazinonyl, pyrazolidinyl, and their various tautomers, as well as unsubstituted and substituted versions thereof. The term "9- or 10-membered heterocyclyl" represents a fully unsaturated or partially unsaturated, bicyclic group, containing 9 or 10 ring atoms, including 1 to 5 heteroatoms independently selected from nitrogen, oxygen and sulfur, which group may be unsubstituted or substituted by one or more of the substituents defined herein. Selected 9- or 10-membered heterocycyl groups contain one nitrogen, oxygen or sulfur ring heteroatom, and optionally contain 1, 2, 3, or 4 additional nitrogen ring atoms and/or 1 additional oxygen or sulfur atom. Examples of 9- or 10-membered heterocyclyl groups include, but are not limited to, benzofuranyl, isobenzofuryl, 2,3-di hydrobenzofuryl, 1,3-benzodioxolyl, dihydrobenzodioxinyl, benzothienyl, indolizinyl, indolyl, isoindolyl, indolinyl, isoindolinyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

The term "aryl" refers to a carbocyclic aromatic moiety (such as phenyl or naphthyl) containing the specified number of carbon atoms, particularly from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl.

As used herein, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 8 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary 5- to 6-membered heteroaryls include, but are not limited to, furanyl, thiophenyl, thienyl, pyrrolyl, imidazolyl, pyrazolyl, triazolyl, tetrazolyl, thiazolyl, isothiazolyl, 1, 2, 3-triazolyl, 1, 2, 4-triazolyl, oxazolyl, isoxazolyl, 1, 2, 3-oxadiazolyl, 1, 2, 5-oxadiazolyl, thiadiazolyl, isothiazolyl, tetrazolyl, pyridinyl, pyridazinyl, pyrazinyl, pyrimidinyl, and triazinyl. Other exemplary heteroaryl groups include, but are not limited to benzofuranyl, isobenzofuryl, 2,3-dihydrobenzofuryl, 1,3-benzodioxolyl, dihydrobenzodioxinyl, benzothienyl, indolizinyl, indolyl, isoindolyl, indolinyl, isoindolinyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, pyrrolopyridinyl, pyrrolopyrimidinyl, imidazopyridinyl, imidazopyrimidinyl, pyrazolopyridinyl, pyrazolopyrimidinyl, benzoxadiazolyl, benzthiadiazolyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl. Suitable substituents for heteroaryl are described in the definition of "optionally substituted."

As used herein "heterocyclic," "heterocycle," "heterocyclyl" groups or grammatical variations thereof include "heteroaryl" and "heterocycloalkyl" groups.

As used herein, the term "cyano" refers to the group —CN.

As used herein, the term "optionally" means that the subsequently described event(s) may or may not occur, and includes both event(s) that occur and event(s) that do not occur.

As used herein, unless otherwise defined, the phrase "optionally substituted" or grammatical variations thereof denote an optional substitution, including multiple degrees of substitution, with one or more substitutent group. The phrase should not be interpreted as duplicative of the substitutions herein described and depicted. Exemplary optional substituent groups include acyl, alkyl, alkylsulfonyl, alkoxy, alkoxycarbonyl, cyano, halogen, haloalkyl, hydroxyl, oxo, amide, sulfamide, urea, amino, substituted amino, acylamino, phenylcarbonyl, dialkylaminosulfonamide, morpholino, sulfonamide, thiourea, nitro, pyrrolidinyl, pyrazolyl, pyrrolyl, phenyl, and tetrazolyl, wherein pyrrolidinyl, pyrazolyl and tetrazolyl can be further substituted with one to three $C_1$-$C_3$alkyl.

"Enantiomerically enriched" refers to products whose enantiomeric excess is greater than zero. For example, enantiomerically enriched refers to products whose enantiomeric excess is greater than about 50% ee, greater than about 75% ee, and greater than about 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 100% ee.

"Diastereomer" refers to a compound having at least two chiral centers.

"Diastereomer excess" or "de" is the excess of one diasteriomer over the others expressed as a percentage.

"Diasteriomerically pure" refers to products whose diasteriomeric excess is 100% de.

"Halo" or "halogen" refers to fluoro, chloro, bromo, or iodo.

"Heteroatom" refers to a nitrogen, sulphur, or oxygen atom.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Oxo" refers to the substituent group =O.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein "co-administration" or "co-administering" as used herein refers to administration of two or more compounds to the same patient. Co-administration of such compounds may be simultaneous or at about the same time (e.g., within the same hour) or it may be within several hours or days of one another. For example, a first compound may be administered once weekly while a second compound is co-administered daily.

As used herein "maximum blood concentration" or "Cmax" means the highest observed concentration of a substance (for example, a compound of formula (I)) in a species' blood after administration of the substance to that species.

As used herein "Area Under the Curve" or "AUC" is the area under the curve in a plot of the concentration of a substance in blood against time. AUC can be a measure of the integral of the instantaneous concentrations during a time interval and has the units mass×time/volume, which can also be expressed as molar concentration×time such as nM×day. AUC is typically calculated by the trapezoidal method (e.g., linear, linear-log). AUC is usually given for the time interval zero to infinity, and other time intervals are indicated (for example $AUC_{(t1-t2)}$ where t1 and t2 are the starting and finishing times for the interval). Thus, as used herein "$AUC_{0-24\,h}$" refers to an AUC over a 24-hour period, and "$AUC_{0-4\,h}$" refers to an AUC over a 4-hour period.

"Dose normalized AUC" or "DNAUC" refers to AUC values which are normalized by dose in mg/kg.

As used herein "confidence interval" or "CI" is an interval in which a measurement or trial falls corresponding to a given probability p where p refers to a 90% or 95% CI and are calculated around either an arithmetic mean, a geometric mean, or a least squares mean. As used herein, a geometric mean is the mean of the natural log-transformed values back-transformed through exponentiation, and the least squares mean may or may not be a geometric mean as well but is derived from the analysis of variance (ANOVA) model using fixed effects.

As used herein the "coefficient of variation (CV)" is a measure of dispersion and it is defined as the ratio of the standard deviation to the mean. It is reported as a percentage (%) by multiplying the above calculation by 100 (% CV).

Drug clearance (CL) is defined as the volume of blood in the vascular compartment cleared of drug per unit time by the processes of metabolism and excretion. Clearance for a drug is constant if the drug is eliminated by first-order kinetics. Drug can be cleared by renal excretion or by metabolism or both. Often the clearance is normalized by the body weight of the mammal being treated and expressed in units of mL/min/kg.

Compounds within the invention may occur in two or more tautometric forms; all such tautomeric forms are included within the scope of the invention.

The invention further provides a pharmaceutical composition (also referred to as pharmaceutical formulation) comprising at least one compound of the invention or pharmaceutically acceptable salt, thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of the present invention or salt thereof with at least one excipient.

PHARMACEUTICAL COMPOSITIONS

Pharmaceutical compositions may be in unit dose form containing a predetermined amount of active ingredient per unit dose. Such a unit may contain a therapeutically effective dose of the compound of the invention such as Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

The present invention provides a method of treatment in a mammal, especially a human, with at least one disease condition targeted by the present compounds. Such treatment comprises the step of administering a therapeutically effective amount of at least one compound of the invention or salt thereof to said mammal, particularly a human. Treatment can also comprise the step of administering a therapeutically effective amount of a pharmaceutical composition containing at least one compound of the invention or salt thereof to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of at least one compound of the invention, as well as salts thereof, may be administered as the raw chemical. Additionally, the active ingredient may be presented as a pharmaceutical composition.

While it is possible that, for use in therapy, a therapeutically effective amount of at least one compound of the invention or salt thereof may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of the invention or salt thereof will be given for the treatment in the range of about 0.1 to 100 mg/kg body weight of recipient (patient, mammal) per day and more usually in the range of 0.1 to 10 mg/kg body weight per day. Acceptable daily dosages may be from about 1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of the invention per se. Similar dosages should be appropriate for treatment (including prophylaxis) of the other conditions referred herein for treatment. In general, determination of appropriate dosing can be readily arrived at by one skilled in medicine or the pharmacy art.

COMBINATIONS

When a compound of the invention is administered for the treatment of cancer, the term "co-administering" and grammatical derivatives thereof as used herein is meant either simultaneous administration or any manner of separate sequential administration of a FAS inhibiting compound, as described herein, and a further active ingredient or ingredients, known to be useful in the treatment of cancer, including, but not limited to, chemotherapy including anti-neoplastic agents and/or radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present FAS inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and *vinca* alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β, 13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β, 10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin Ill, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)—O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-respectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H)pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b] quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of Formula A following, currently under development, including the racemic mixture (R,S) form as well as the R and S enantiomers:

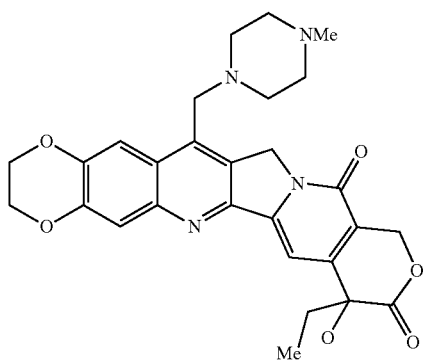

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681, 835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Letrozole (trade name Femara) is an oral non-steroidal aromatase inhibitor for the treatment of hormonally-responsive breast cancer after surgery. Estrogens are produced by the conversion of androgens through the activity of the aromatase enzyme. Estrogens then bind to an estrogen receptor, which causes cells to divide. Letrozole prevents the aromatase from producing estrogens by competitive, reversible binding to the heme of its cytochrome P450 unit. The action is specific, and letrozole does not reduce production of mineralo- or corticosteroids.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and Bennett, C. F. and Cowsert, L. M. BioChim. Biophys. Acta, (1999) 1489(1):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$, beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Pazopanib which commercially available as VOTRIENT® is a tyrosine kinase inhibitor (TKI). Pazopanib is presented as the hydrochloride salt, with the chemical name 5-[[4-[(2,3-dimethyl-2H-indazol-6-yl)methylamino]-2-pyrimidinyl]amino]-2-methylbenzenesulfonamide monohydrochloride. Pazoponib is approved for treatment of patients with advanced renal cell carcinoma.

Bevacisumab which is commercially available as AVASTIN® is a humanized monoclonal antibody that blocks VEGF-A. AVASTIN® is approved form the treatment of various cancers including colorectal, lung, breast, kidney, and glioblastomas.

mTOR inhibitors include but are not limited to rapamycin (FK506) and rapalogs, RAD001 or everolimus (Afinitor), CCI-779 or temsirolimus, AP23573, AZD8055, WYE-354, WYE-600, WYE-687 and Pp121.

Everolimus is sold as Afinitor® by Novartis and is the 40-O-(2-hydroxyethyl) derivative of sirolimus and works similarly to sirolimus as an mTOR (mammalian target of rapamycin) inhibitor. It is currently used as an immunosuppressant to prevent rejection of organ transplants and treatment of renal cell cancer. Much research has also been conducted on everolimus and other mTOR inhibitors for use in a number of cancers. It has the following chemical structure (Formula B) and chemical name:

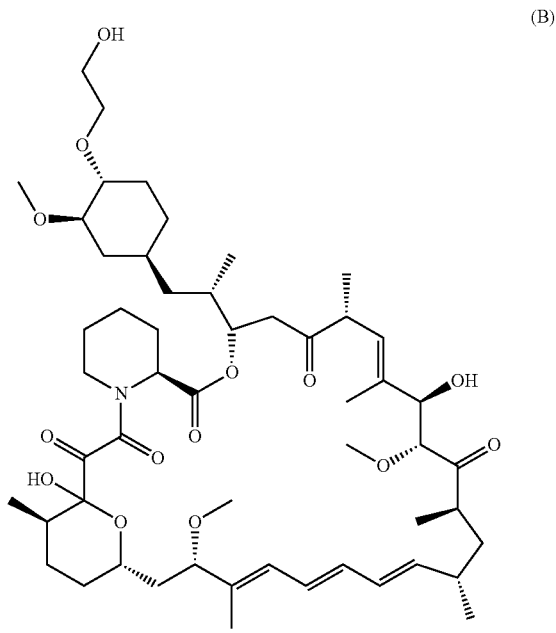

dihydroxy-12-[(2R)-1-[(1 S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo [30.3.1.0$^{4,9}$]hexatriaconta-16,24,26,28-tetraene-2,3,10,14, 20-pentone.

Bexarotene is sold as Targretin® and is a member of a subclass of retinoids that selectively activate retinoid X receptors (RXRs). These retinoid receptors have biologic activity distinct from that of retinoic acid receptors (RARs). The chemical name is 4-[1-(5,6,7,8-tetrahydro-3,5,5,8,8-pentamethyl-2-naphthalenyl) ethenyl] benzoic acid. Bexarotene is used to treat cutaneous T-cell lymphoma (CTCL, a type of skin cancer) in people whose disease could not be treated successfully with at least one other medication.

Sorafenib marketed as Nexavar® is in a class of medications called multikinase inhibitors. Its chemical name is 4-[4-[[4-chloro-3-(trifluoromethyl)phenyl]carbamoylamino]phenoxy]-N-methyl-pyridine-2-carboxamide. Sorafenib is used to treat advanced renal cell carcinoma (a type of cancer that begins in the kidneys). Sorafenib is also used to treat unrespectable hepatocellular carcinoma (a type of liver cancer that cannot be treated with surgery).

Agents used in immunotherapeutic regimens may also be useful in combination with the compounds of the present invention. There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Examples of erbB inhibitors include lapatinib, erlotinib, and gefitinib. Lapatinib, N-(3-chloro-4-{[(3-fluorophenyl) methyl]oxy}phenyl)-6-[5-({[2-(methylsulfonyl)ethyl] amino}methyl)-2-furanyl]-4-quinazolinamine (represented by Formula C, as illustrated), is a potent, oral, small-molecule, dual inhibitor of erbB-1 and erbB-2 (EGFR and HER2) tyrosine kinases that is approved in combination with capecitabine for the treatment of HER2-positive metastatic breast cancer.

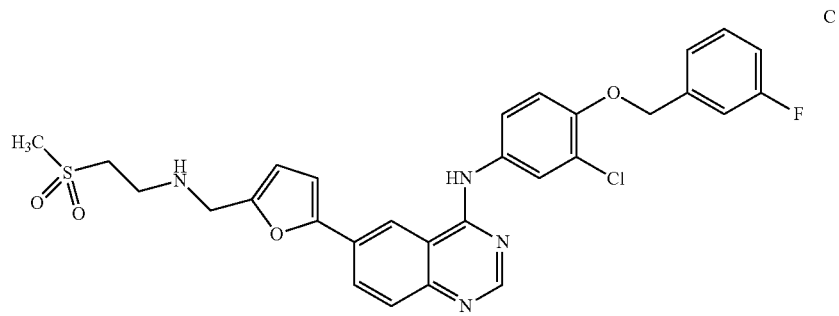 [SMILES: CS(=O)(=O)CCNCc1ccc(-c2ccc3ncnc(Nc4ccc(OCc5cccc(F)c5)c(Cl)c4)c3c2)o1]

Erlotinib, N-(3-ethynylphenyl)-6,7-bis{[2-(methyloxy)ethyl]oxy}-4-quinazolinamine Commercially available under the tradename Tarceva) is represented by Formula D, as illustrated:

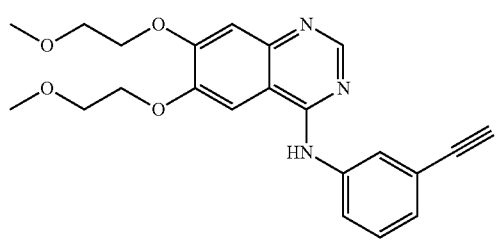

The free base and HCl salt of erlotinib may be prepared, for example, according to U.S. Pat. No. 5,747,498, Example 20.

Gefitinib, 4-quinazolinamine, N-(3-chloro-4-fluorophenyl)-7-methoxy-6-[3-4-morpholin)propoxy] is represented by Formula E, as illustrated:

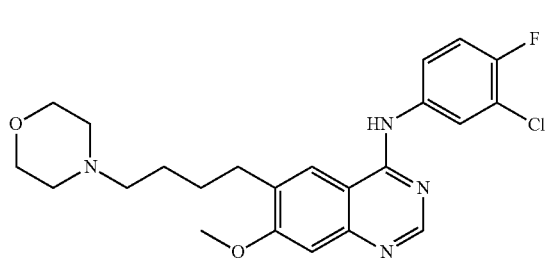

Gefitinib, which is commercially available under the trade name IRESSA® (Astra-Zenenca) is an erbB-1 inhibitor that is indicated as monotherapy for the treatment of patients with locally advanced or metastatic non-small-cell lung cancer after failure of both platinum-based and docetaxel chemotherapies. The free base, HCl salts, and diHCl salts of gefitinib may be prepared according to the procedures of International Patent Application No. PCT/GB96/00961, filed Apr. 23, 1996, and published as WO 96/33980 on Oct. 31, 1996.

Trastuzumab (HEREPTIN®) is a humanized monoclonal antibody that binds to the HER2 receptor. It original indication is HER2 positive breast cancer.

Cetuximab (ERBITUX®) is a chimeric mouse human antibody that inhibits epidermal growth factor receptor (EGFR).

Pertuzumab (also called 2C4, trade name Omnitarg) is a monoclonal antibody. The first of its class in a line of agents called "HER dimerization inhibitors". By binding to HER2, it inhibits the dimerization of HER2 with other HER receptors, which is hypothesized to result in slowed tumor growth. Pertuzumab is described in WO01/00245 published Jan. 4, 2001.

Rituximab is a chimeric monoclonal antibody which is sold as RITUXAN® and MABTHERA®. Rituximab binds to CD20 on B cells and causes cell apoptosis. Rituximab is administered intravenously and is approved for treatment of rheumatoid arthritis and B-cell non-Hodgkin's lymphoma.

Ofatumumab is a fully human monoclonal antibody which is sold as ARZERRA®. Ofatumumab binds to CD20 on B cells and is used to treat chronic lymphocytic leukemia (CLL; a type of cancer of the white blood cells) in adults who are refractory to treatment with fludarabine (Fludara) and alemtuzumab (Campath).

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/111 trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of the invention and/or a pharmaceutically acceptable salt, hydrate, solvate or pro-drug thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

EXPERIMENTALS

Preparation

The derivatives described herein were prepared by the general methods outlined in WO2011/103546A1, herein incorporated by reference in its entirety, and described in detail below.

Example 1

(S)-3-((1-(cyclopropanecarbonyl)pyrrolidin-3-yl)methyl)-4-(2-fluoro-4-(3-methylquinolin-7-yl)phenyl)-1H-1,2,4-triazol-5(4H)-one

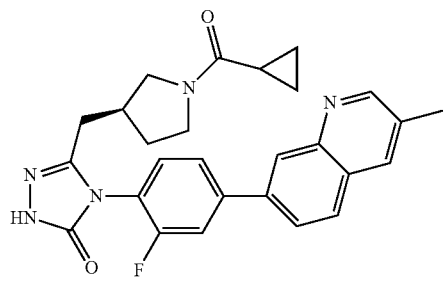 [SMILES: Cc1cnc2cc(-c3ccc(-n4c(C[C@@H]5CCN(C(=O)C6CC6)C5)n[nH]c4=O)c(F)c3)ccc2c1]

a) 1,1-dimethylethyl (3S)-3-[2-(ethyloxy)-2-oxoethyl]-1-pyrrolidinecarboxylate

To a 2 L round bottom flask containing ((3S)-1-{[(1,1-dimethylethyl)oxy]carbonyl}-3-pyrrolidinyl)acetic acid (97.0 g, 423 mmol) and diethyl ether (800 mL) was added N-(3-dimethylaminopropyl)-N'-ethylcarbodiimide hydrochloride (89.0 g, 465 mmol), 4-dimethylaminopyridine (5.17 g, 42.3 mmol), and ethanol (54.0 mL, 931 mmol). The reaction flask was equipped with an overhead stirrer and the white reaction mixture was stirred overnight at room temperature. Analysis of an aliquot by LCMS indicated the reaction had proceeded to completion. The reaction mixture was transferred to a 2 L separatory funnel. Residual precipitate in the flask was dissolved with 1N aq NaHSO$_4$ and was added to the separatory funnel. The aqueous layer was separated and the organic layer was washed with 1N aq NaHSO$_4$, saturated aq sodium bicarbonate, and brine. The organic layer was dried over sodium sulfate, filtered, and concentrated in vacuo to afford the title compound as a clear yellow gel (96.6 g) which was carried forward without purification. MS(ES)+ m/e 258.0 [M+H]$^+$.

b) 1,1-dimethylethyl (3S)-3-(2-hydrazino-2-oxoethyl)-1-pyrrolidinecarboxylate

To a 2 L round bottom flask containing the crude 1,1-dimethylethyl (3S)-3-[2-(ethyloxy)-2-oxoethyl]-1-pyrrolidinecarboxylate (96.2 g) and ethanol (700 mL) was added hydrazine monohydrate (65% by weight, 100 mL). The reaction flask was equipped with an overhead stirrer and the reaction mixture was stirred overnight at 75° C. Analysis of an aliquot by LCMS indicated near complete conversion of the starting material to the desired product. The solution was cooled to room temperature, concentrated in vacuo, and azeotroped with ethanol (500 mL). The resulting gel was diluted with dichloromethane (500 mL), dried over sodium sulfate, and filtered. The filtrate was concentrated in vacuo to afford the title compound as a clear gel (98.7 g) which was carried forward without purification. MS(ES)+ m/e 244.1 [M+H]$^+$.

c) 1,1-dimethylethyl (3S)-3-[2-(2-{[(4-bromo-2-fluorophenyl)amino]carbonyl}hydrazino)-2-oxoethyl]-1-pyrrolidinecarboxylate To a 2 L round bottom flask containing the crude 1,1-dimethylethyl (3S)-3-(2-hydrazino-2-oxoethyl)-1-pyrrolidinecarboxylate (98.7 g) in dichloromethane (400 mL) was added a solution of 4-bromo-2-fluoro-1-isocyanatobenzene (88.0 g, 406 mmol) in dichloromethane (400 mL). The reaction flask was equipped with an overhead stirrer and the reaction mixture was stirred at room temperature for 1 h, at which point the clear solution had turned to a milky white suspension. The solid precipitate was collected via gravity filtration, washed with cold dichloromethane (2×50 mL), and dried in a vacuum oven (50° C.) for overnight to afford the title compound as a white, pure solid (167.4 g, 86% over the 3 steps). MS(ES)+ m/e 459.2, 461.1 [M+H]$^+$.

d) 1,1-dimethylethyl (3S)-3-{[4-(4-bromo-2-fluorophenyl)-5-oxo-4,5-dihydro-1H-1,2,4-triazol-3-yl]methyl}-1-pyrrolidinecarboxylate To a 2 L round bottom flask containing 1,1-dimethylethyl (3S)-3-[2-(2-{[(4-bromo-2-fluorophenyl)amino]carbonyl}hydrazino)-2-oxoethyl]-1-pyrrolidinecarboxylate (25.0 g, 54.4 mmol) was added was potassium carbonate (40.0 g, 289 mmol), water (1000 mL), and 1-propanol (100 mL). A reflux condenser with a nitrogen bubbler was attached and the reaction mixture was stirred at 140° C. for 20 h. The reaction mixture was cooled to room temperature, filtered, and concentrated in vacuo. The residue was taken up in 1N aq NaOH (125 mL). Di-tert-butyl dicarbonate (6.0 g, 28 mmol) was added and the reaction stirred at room temperature for 72 h. Analysis of an aliquot by LCMS indicated the reaction had progressed to 70% completion. Addition of more di-tert-butyl dicarbonate (2.0 g, 9.3 mmol) enabled the reaction to progress to >95% completion, with a small amount (<5%) of bis-protected material (MW=540) observed. The reaction was adjusted to pH=6-7 with the addition of 1N aq HCl. The reaction was transferred to a separatory funnel and washed with ethyl acetate (2×200 mL). The combined organic layers were dried over sodium sulfate, filtered, and concentrated in vacuo. Purification of the residue by silica gel chromatography (0-10% methanol:dichloromethane) afforded the title compound (12.2 g, 48%). MS(ES)+ m/e 440.8, 442.8 [M+H]$^+$.

e) 4-(4-bromo-2-fluorophenyl)-5-{[(3S)-1-(cyclopropylcarbonyl)-3-pyrrolidinyl]methyl}-2,4-dihydro-3H-1,2,4-triazol-3-one To a 1 L round bottom flask containing 1,1-dimethylethyl (3S)-3-{[4-(4-bromo-2-fluorophenyl)-5-oxo-4,5-dihydro-1H-1,2,4-triazol-3-yl]methyl}-1-pyrrolidinecarboxylate (26.5 g, 60.1 mmol) was added 4N HCl in dioxane (100 mL, 400 mmol). The reaction mixture was stirred at room temperature for 1 hour and then concentrated in vacuo. Dichloromethane (300 mL) was added to the flask and the solution was cooled with an ice bath. N,N-diisopropylethylamine (42.0 mL, 240 mmol) was added to the flask. Cyclopropancarbonyl chloride (5.00 mL, 54.6 mmol) in dichloromethane (50 mL) was then added to the flask via an addition funnel. After 2 h, analysis of an aliquot by LCMS indicated the reaction had progressed-80%. As the reaction mixture temperature was maintained at 0° C., cyclopropancarbonyl chloride (1.00 mL, 10.9 mmol) in dichloromethane (20 mL) was added via an addition funnel. After 1 h, analysis of an aliquot by LCMS indicated the reaction had progressed ~97%. Cyclopropancarbonyl chloride (0.200 mL, 2.18 mmol) in dichloromethane (5 mL) was added via pipette. After 1 h, analysis of an aliquot by LCMS indicated the reaction had progressed to completion. The reaction mixture was diluted with dichloromethane (200 mL) and transferred to a separatory funnel. The organic layer was washed with water, brine, and saturated aq $NH_4Cl$ and then dried over sodium sulfate, filtered, and concentrated in vacuo. Purification of the residue by silica gel chromatography (0-10% methanol:ethyl acetate) afforded the title product (16.5 g, 67%). MS(ES)+ m/e 409.0, 410.9 $[M+H]^+$.

f) 7-bromo-3-methylquinoline

A solution of KOH (5.61 g, 100 mmol) dissolved in ethanol (50 mL) was added drop wise to a mixture of 2-amino-4-bromobenzaldehyde (60.6 g, 303 mmol) and propionaldehyde (17.6 g, 303 mmol) in absolute ethanol (200 mL) under nitrogen. The mixture was heated to reflux, and then maintained at reflux for 3 h. After cooling to room temperature, the reaction mixture was concentrated to remove the ethanol, then water was added and the mixture was extracted with methylene chloride (3×100 mL). The combined organic layers were washed with water, dried over sodium sulfate, and concentrated in vacuo. The crude material was triturated from diethyl ether to provide the title product (48.6 g, 219 mmol, 72% yield) as a light brown solid. MS(ES) m/e 221.9, 223.9 $[M+H]^+$ (bromine pattern).

g) (S)-3-((1-(cyclopropanecarbonyl)pyrrolidin-3-yl)methyl)-4-(2-fluoro-4-(3-methylquinolin-7-yl)phenyl)-1H-1,2,4-triazol-5(4H)-one A 10 mL microwaveable vial was charged with (S)-4-(4-bromo-2-fluorophenyl)-3-((1-(cyclopropanecarbonyl)pyrrolidin-3-yl)methyl)-1H-1,2,4-triazol-5(4H)-one (150 mg, 0.367 mmol), potassium acetate (150 mg, 1.53 mmol), bis(pinacolato)diboron (100 mg, 0.394 mmol), $PdCl_2(dppf)$-$CH_2Cl_2$ adduct (50 mg, 0.061 mmol), and 1,4-dioxane (4 mL). The vial was capped, purged with nitrogen, and stirred at 100° C. for 16 h. The solution was cooled to room temperature. Analysis of an aliquot by LCMS displayed the desired boronate ester (MW=456) along with the corresponding boronic acid intermediate (MW=374). To the vial was added 7-bromo-3-methylquinoline (90 mg, 0.405 mmol) and 2M aq potassium carbonate (2.00 mL). The vial was capped, purged with nitrogen, and stirred at 100° C. After 1 hour, the solution was cooled to room temperature. The dioxane layer was decanted via pipette and placed into a separatory funnel. The organics were extracted using ethyl acetate (40 mL) and water (20 mL). The ethyl acetate layer was removed and the aqueous layer was extracted with ethyl acetate (10 mL). The combined organic layers were washed with brine (1×), dried over sodium sulfate and approximately 60 mg of Silicycle Si-thiol resin, filtered, and concentrated in vacuo. Purification of the residue by silica gel chromatography (0-10% methanol:dichloromethane) afforded the title compound (61 mg, 35% yield). MS(ES)+ m/e 472.2 $[M+H]^+$.

Example 2

(S)-4-(4-(3-chloroquinolin-7-yl)-2-fluorophenyl)-3-((1-(cyclopropanecarbonyl)pyrrolidin-3-yl)methyl)-1H-1,2,4-triazol-5(4H)-one

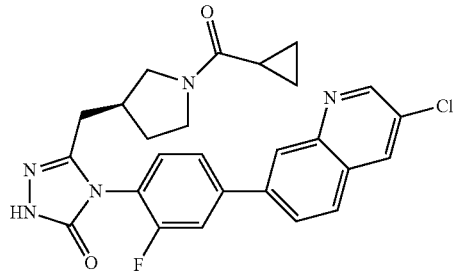 [SMILES: O=C(C1CC1)N1CC[C@@H](Cc2n[nH]c(=O)n2-c2ccc(-c3ccc4cc(Cl)cnc4c3)cc2F)C1]

a) 7-bromo-3-chloroquinoline

A mixture of 2-chloro-1,1-diethoxyethane (4.50 mL, 30.0 mmol), 2-amino-4-bromobenzaldehyde (3.00 g, 15.0 mmol), and p-toluenesulfonic acid monohydrate (0.285 g, 1.500 mmol) in toluene (50 mL) was heated at 110° C. for 3 hours using a Dean/Stark trap. The solvent was then evaporated and the residue partitioned between ethyl acetate and saturated aq $NaHCO_3$. The aqueous layer was extracted with ethyl acetate and the combined organic extracts were evaporated onto silica gel and purified by flash chromatography (20-50% dichloromethane/hexanes) to give the title product (1.97 g, 8.12 mmol, 54% yield) as a yellow solid. MS (ES+) m/e 241.8/243.8 Br pattern $[M+H]^+$; $^1H$ NMR (400 MHz, DMSO-$d_6$) δ ppm 7.85 (dd, J=8.84, 2.02 Hz, 1H) 7.98 (d, J=8.59 Hz, 1H) 8.29 (d, J=1.77 Hz, 1H) 8.65 (d, J=2.02 Hz, 1H) 8.94 (d, J=2.53 Hz, 1H).

b) (S)-4-(4-(3-chloroquinolin-7-yl)-2-fluorophenyl)-3-((1-(cyclopropanecarbonyl)pyrrolidin-3-yl)methyl)-1H-1,2,4-triazol-5(4H)-one Following the procedure described in Example 1g with 7-bromo-3-chloroquinoline (1.01 eq) provided the title compound (56 mg, 31%). MS(ES)+ m/e 492.4 $[M+H]^+$.

Example 3

(S)-3-((1-(cyclopropanecarbonyl) pyrrolidin-3-yl)methyl)-4-(2-fluoro-4-(3-fluoroquinolin-7-yl)phenyl)-1H-1,2,4-triazol-5(4H)-one

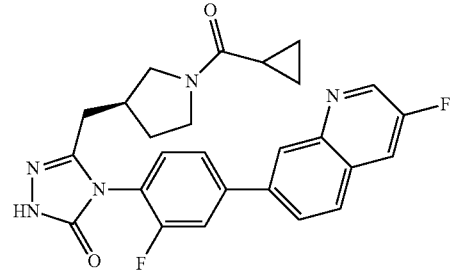 [SMILES: O=C(C1CC1)N1CC[C@@H](Cc2n[nH]c(=O)n2-c2ccc(-c3ccc4cc(F)cnc4c3)cc2F)C1]

a) 2-(7-bromoquinolin-3-yl)isoindoline-1,3-dione

A mixture of 2-(2,2-diethoxyethyl)isoindoline-1,3-dione (3.16 g, 12.00 mmol), 2-amino-4-bromobenzaldehyde (2 g, 10.00 mmol) and p-toluenesulfonic acid monohydrate (1.902 g, 10.00 mmol) in toluene (60 mL) was heated under reflux using Dean-Stark apparatus overnight. A very dark/black solid precipitated overnight and was collected, washed with toluene and hexanes, then dissolved in chloroform fortified with DMF. The mixture was washed with aq. NaHCO$_3$ solution (2×), ensuring any precipitate was dissolved in additional chloroform during separation. The organic layer was dried (sodium sulfate) and evaporated onto silica gel. Purification by flash chromatography (0-2% methanol in dichloromethane) afforded the title compound (1.6 g, 45%). $^1$H NMR (400 MHz, DMSO-d$_6$) δ ppm 9.05 (d, 1H), 8.57 (d, J=2.3 Hz, 1H), 8.35 (d, J=1.8 Hz, 1H), 8.11 (d, J=8.6 Hz, 1H), 8.09-8.02 (m, 2H), 8.02-7.93 (m, 2H), 7.87 (dd, J=1.9, 8.7 Hz, 1H).

b) 7-bromoquinolin-3-amine

A suspension of 2-(7-bromoquinolin-3-yl)isoindoline-1,3-dione (10 g, 28.3 mmol) in ethanol (200 mL) was treated with hydrazine (1.777 mL, 56.6 mmol) then heated under reflux for 1 h. The mixture was allowed to cool, the precipitate was collected and washed with a little ethanol, and the filtrate was evaporated as a grey solid. The isolated solid was dissolved in warm ethanol and adsorbed onto silica gel. Purification of the solid by silica gel chromatography (50-100% ethyl acetate/hexanes) afforded the title compound (3.5 g, 56%). $^1$H NMR (400 MHz, DMSO-d$_6$) δ ppm 5.83 (s, 2H) 7.14 (d, J=2.53 Hz, 1H) 7.49 (dd, J=8.84, 2.02 Hz, 1H) 7.54-7.65 (m, 1H) 7.94 (d, J=1.77 Hz, 1H) 8.46 (d, J=2.78 Hz, 1H).

c) 7-bromo-3-fluoroquinoline

To a 100 mL round bottom flask containing a solution of 7-bromoquinolin-3-amine (2.00 g, 8.97 mmol) in chlorobenzene (20 mL) was added borontrifluoride dihydrate (0.900 mL, 13.6 mmol) dropwise via a syringe. The solution was stirred under nitrogen as the flask temperature was raised to 50° C. Tert-butyl nitrite (1.185 mL, 8.97 mmol) was added slowly dropwise (over 15 min) to the reaction mixture via an addition funnel. The flask temperature was raised to 100° C. and the reaction mixture was stirred under nitrogen for 2 h. The reaction mixture was cooled to room temperature and then poured into a flask containing ice and saturated aq sodium bicarbonate (~100 mL). The reaction flask was washed with chloroform and dichloromethane and the organic washes (~100 mL) were transferred to a separatory funnel along with the aqueous layer. The organic layer was removed and the aqueous layer was washed with chloroform (3×). The combined organic layers were washed with brine, dried over sodium sulfate, filtered, and concentrated in vacuo. Purification of the residue by silica gel chromatography (20-50% dichloromethane:hexanes) afforded the title compound (731 mg, 36%). MS(ES)+ m/e 227.9 [M+H]$^+$.

d) (S)-3-((1-(cyclopropanecarbonyl) pyrrolidin-3-yl) methyl)-4-(2-fluoro-4-(3-fluoroquinolin-7-yl)phenyl)-1H-1,2,4-triazol-5(4H)-one Following the procedure described in Example 1g with 7-bromo-3-fluoroquinoline (0.9 eq) provided the title compound as an off white solid (40 mg, 34%). Instead of an aqueous workup, the decanted dioxane layer was directly absorbed onto a pad of silica gel. Silica gel chromatography (0-10% methanol:dichloromethane) and reverse phase HPLC (10-80% acetonitrile/water+0.1% NH$_4$OH) were both utilized in purifying this compound. MS(ES)+ m/e 475.8 [M+H]$^+$.

Example 4

(S)-4-(2-fluoro-4-(3-fluoroquinolin-7-yl)phenyl)-3-((1-propionylpyrrolidin-3-yl)methyl)-1H-1,2,4-triazol-5(4H)-one

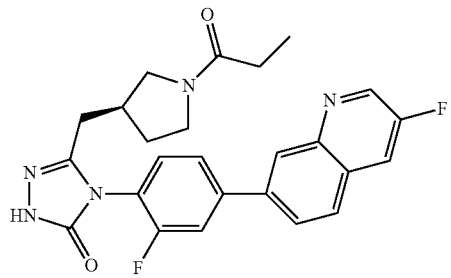 [SMILES: CCC(=O)N1CC[C@@H](Cc2n[nH]c(=O)n2-c2ccc(-c3ccc4cc(F)cnc4c3)cc2F)C1]

a) 1,1-dimethylethyl (3S)-3-[2-(ethyloxy)-2-oxoethyl]-1-pyrrolidinecarboxylate To a 1 L round bottom flask was added ((3S)-1-{[(1,1-dimethylethyl)oxy]carbonyl}-3-pyrrolidinyl)acetic acid (20 g, 87 mmol) and diethyl ether (200 mL). The solution was stirred for 1 minute and then N-(3-dimethylaminopropyl)-N'-ethylcarbodiimide hydrochloride (18 g, 94 mmol), 4-dimethylaminopyridine (1.00 g, 8.19 mmol), and ethanol (11 mL, 188 mmol) were added. A nitrogen bubbler was attached to the flask and the reaction mixture was stirred overnight at room temperature. Diethyl ether (200 mL) and water (200 mL) were added to the mixture, and once the precipitated solid was dissolved, the flask contents were poured into a separatory funnel. The aqueous layer was separated and the organic layer was washed with saturated aq NH$_4$Cl, saturated sodium bicarbonate, and then brine. The organic layer was dried over sodium sulfate, filtered, and concentrated in vacuo to afford the title compound (19.1 g) which was carried forward without purification. MS(ES)+ m/e 257.8 [M+H]$^+$.

b) ethyl [(3S)-1-propanoyl-3-pyrrolidinyl]acetate

To a 500 mL round bottom flask containing the 1,1-dimethylethyl (3S)-3-[2-(ethyloxy)-2-oxoethyl]-1-pyrrolidinecarboxylate (19.1 g) was slowly added 4M HCl in dioxane (100 mL, 400 mmol). The resulting solution was stirred at room temperature for 1 h. The solution was then concentrated in vacuo to yield a beige solid. The solid was suspended in dichloromethane (DCM) (300 mL) and was treated with N,N-diisopropylethylamine (25.9 mL, 148 mmol) while stirring at room temperature. To the resulting yellow solution was added dropwise propanoyl chloride (6.87 g, 74.2 mmol). The reaction was stirred for 30 minutes at room temperature, at which point analysis of an aliquot by LCMS indicated that the reaction had proceeded to completion. The solution was diluted with DCM (500 mL) and was successively washed with saturated aq ammonium chloride (400 mL), saturated aq sodium bicarbonate (400 mL), and brine (400 mL). The organic layer was dried over sodium sulfate, filtered, and concentrated to dryness in vacuo to afford the title compound as a yellow oil (16 g), which was carried forward without purification. MS(ES)+ m/e 213.9 [M+H]⁺.

c) 2-[(3S)-1-propanoyl-3-pyrrolidinyl]acetohydrazide

To a 1 L round bottom flask containing the ethyl [(3S)-1-propanoyl-3-pyrrolidinyl]acetate (16 g) was added ethanol (100 mL) and hydrazine monohydrate (70 mL, 940 mmol). A reflux condenser with a nitrogen bubbler was attached to the flask. The flask was placed in an oil bath and heated to 80° C. with stirring overnight. Analysis of an aliquot by LCMS indicated the reaction had proceeded to completion. The solution was cooled to room temperature, concentrated in vacuo, and azeotroped with ethanol (5×100 mL). The resulting oil was diluted with DCM (300 mL) and passed through a plug of magnesium sulfate. The magnesium sulfate was washed with DCM (300 mL). The combined filtrate was concentrated in vacuo to afford the title compound as a clear oil (15 g) which was carried forward without purification. MS(ES)+ m/e 199.9 [M+H]⁺.

d) N-(4-bromo-2-fluorophenyl)-2-{[(3S)-1-propanoyl-3-pyrrolidinyl]acetyl}hydrazinecarboxamide To a 1 L round bottom flask containing the crude 2-[(3S)-1-propanoyl-3-pyrrolidinyl]acetohydrazide (15 g) in dichloromethane (100 mL) was added 4-bromo-2-fluorophenylisocyanate (16.2 g, 75.0 mmol) dropwise via pipette. Additional dichloromethane (60 mL) was used to rinse out the vial containing the isocyanate and was also added to the reaction flask. The solution turned to a stirring white precipitate within 10 min. The flask was placed under a nitrogen bubbler and stirred at room temperature. After 2 hours, the white precipitate had increased such that stirring was difficult. Analysis of an aliquot by LCMS indicated no starting hydrazide remained. The solution was concentrated in vacuo. The solid was washed with hexanes (500 mL), filtered, and dried under vacuum for 48 h to afford the title compound as white solid (30.5 g), which was carried forward without purification. MS(ES)+ m/e 414.9, 416.9 [M+H]⁺.

e) 4-(4-bromo-2-fluorophenyl)-5-{[(3S)-1-propanoyl-3-pyrrolidinyl]methyl}-2,4-dihydro-3H-1,2,4-triazol-3-one To a 2 L round bottom flask containing the crude N-(4-bromo-2-fluorophenyl)-2-{[(3S)-1-propanoyl-3-pyrrolidinyl]acetyl}hydrazinecarboxamide (30.5 g) and potassium carbonate (51 g, 370 mmol) was added water (1000 mL) and 1-propanol (100 mL). A reflux condenser with a nitrogen bubbler was attached and the reaction mixture was stirred at 140° C. After 16 h, the reaction mixture was cooled and then filtered. The filtrate was adjusted to a pH=6-7 with the addition of 1N aq HCl. The desired product was extracted from the aqueous layer with dichloromethane (3×). The combined organic layers were dried over sodium sulfate, filtered, and concentrated in vacuo. Purification of the residue by silica gel chromatography (0-10% methanol:ethyl acetate) afforded the title compound as a white solid (12 g, 34% over the 5 steps). MS(ES)+ m/e 396.7, 398.9 [M+H]⁺.

f) (S)-4-(2-fluoro-4-(3-fluoroquinolin-7-yl)phenyl)-3-((1-propionylpyrrolidin-3-yl)methyl)-1H-1,2,4-triazol-5(4H)-one To a 10 mL microwaveable vial were added 7-bromo-3-fluoroquinoline (260 mg, 1.15 mmol), bis(pinacolato)diboron (310 mg, 1.22 mmol), potassium acetate (390 mg, 3.97 mmol), PdCl₂(dppf)-CH₂Cl₂ adduct (75 mg, 0.092 mmol), and 1,4-dioxane (6 mL). The vial was capped and purged with nitrogen, and the reaction mixture was stirred at 100° C. for 1 h. Analysis of an aliquot by LCMS indicated formation of the desired quinoline boronic acid intermediate. To the vial was added (S)-4-(4-bromo-2-fluorophenyl)-3-((1-propionylpyrrolidin-3-yl)methyl)-1H-1,2,4-triazol-5(4H)-one (450 mg, 1.13 mmol) and 2M aq potassium carbonate (3.00 mL). The vial was capped and purged with nitrogen, and the reaction mixture was stirred at 100° C. After 2 hours, the solution was cooled to room temperature and adjusted to pH=6-7 with 1N aq HCl. The solution was diluted with dichloromethane (70 mL) and transferred to a separatory funnel. The organic solution was washed with water (50 mL) and the aqueous layer was extracted with dichloromethane (50 mL). The combined organic layers were washed with brine (50 mL), dried over sodium sulfate and approximately 100 mg of Silicycle Si-thiol resin, filtered, and concentrated in vacuo. Purification of the residue by flash chromatography (0-10% methanol:ethyl acetate) afforded the title compound as a cream colored solid (394 mg, 74% yield). MS(ES)+ m/e 463.8 [M+H]⁺.

Example 5

(S)-4-(2-fluoro-4-(3-methylquinolin-7-yl)phenyl)-3-((1-propionylpyrrolidin-3-yl)methyl)-1H-1,2,4-triazol-5(4H)-one

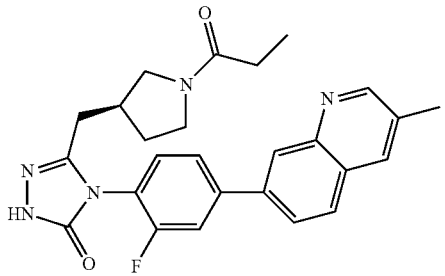 [SMILES: CCC(=O)N1CC[C@@H](Cc2n[nH]c(=O)n2-c2ccc(-c3ccc4cc(C)cnc4c3)cc2F)C1]

a) Following the procedure described in Example 4f with 7-bromo-3-methylquinoline (1.05 eq) provided the title compound as a cream colored solid (335 mg, 62%). MS(ES)+m/e 460.5 [M+H]⁺.

Example 6

(S)-4-(4-(3-chloroquinolin-7-yl)-2-fluorophenyl)-3-((1-propionylpyrrolidin-3-yl)methyl)-1H-1,2,4-triazol-5(4H)-one

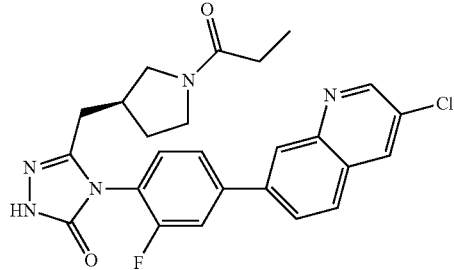 [SMILES: CCC(=O)N1CC[C@@H](Cc2n[nH]c(=O)n2-c2ccc(-c3ccc4cc(Cl)cnc4c3)cc2F)C1]

a) Following the procedure described in Example 4f with 7-bromo-3-chloroquinoline (1.00 eq) provided the title compound as a cream colored solid (127 mg, 58%). MS(ES)+ m/e 480.1 [M+H]+.

Example 7

(S)-4-(2-fluoro-4-(3-methylquinolin-7-yl)phenyl)-1-methyl-3-((1-propionylpyrrolidin-3-yl)methyl)-1H-1,2,4-triazol-5(4H)-one

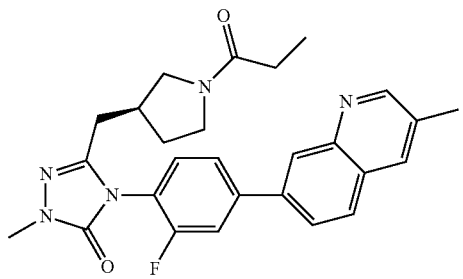

a) (S)-4-(4-bromo-2-fluorophenyl)-1-methyl-3-((1-propionylpyrrolidin-3-yl)methyl)-1H-1,2,4-triazol-5(4H)-one A dried 2-neck 100 mL round bottom flask was placed under a nitrogen atmosphere and charged with (S)-4-(4-bromo-2-fluorophenyl)-3-((1-propionylpyrrolidin-3-yl)methyl)-1H-1,2,4-triazol-5(4H)-one (3.00 g, 7.55 mmol). N,N-Dimethylformamide (DMF) (40 mL) was added, followed by iodomethane (0.700 mL, 11.2 mmol). This solution was cooled to 0° C. with an ice bath. Sodium hydride (60% dispersion in mineral oil, 0.54 g, 13.5 mmol) was added portionwise. The reaction mixture was kept under nitrogen and stirred, while the ice bath was allowed to warm to room temperature. After 2 hours, analysis of an aliquot by LCMS indicated the reaction had proceeded to completion. Water (14 mL) was added slowly to the reaction mixture, which was then transferred to a separatory funnel containing ethyl acetate (100 mL) and water (50 mL). The organic layer was separated and set aside. The aqueous layer was adjusted to pH=6 with addition of 1N aq HCl. The aqueous layer was washed with ethyl acetate (2×). The combined organic layers were washed with a 1:1 water:brine solution (5×). The organic layer was dried over sodium sulfate, filtered, and concentrated in vacuo to afford the title compound as a white solid (2.95 g), which was carried forward without purification. MS(ES)+ m/e 411.3, 413.3 [M+H]+.

b) (S)-4-(2-fluoro-4-(3-methylquinolin-7-yl)phenyl)-1-methyl-3-((1-propionylpyrrolidin-3-yl)methyl)-1H-1,2,4-triazol-5(4H)-one To a 500 mL round bottom flask containing the crude (S)-4-(4-bromo-2-fluorophenyl)-1-methyl-3-((1-propionylpyrrolidin-3-yl)methyl)-1H-1,2,4-triazol-5(4H)-one (2.95 g), was added bis(pinacolato)diboron (2.00 g, 7.88 mmol), potassium acetate (3.00 g, 30.6 mmol), PdCl$_2$(dppf)-CH$_2$Cl$_2$ adduct (0.50 g, 0.61 mmol), and 1,4-dioxane (30 mL). A condenser was attached and the solution was stirred at 100° C. for 1 h. Analysis of an aliquot by LCMS indicated the starting material had been consumed and the desired boronic acid intermediate was present. The reaction mixture was cooled to room temperature, and the flask was charged with 7-bromo-3-methylquinoline (1.6 g, 7.2 mmol), and 2M aq potassium carbonate (15.00 mL). The reaction mixture was stirred at 100° C. for 1 h and then was cooled to room temperature. The solution was adjusted to pH=7 with the addition of 1N aq HCl. The desired product was extracted with ethyl acetate (2×200 mL). The combined organic layers were dried over sodium sulfate and approximately 1 g of Silicycle Si-thiol resin, filtered, and concentrated in vacuo. Purification of the residue by silica gel chromatography (0-10% methanol:dichloromethane) and then by reverse phase HPLC (35% acetonitrile/65% 0.3M aq ammonium formate) afforded the title compound as a white solid (2.3 g, 64% yield over two steps). MS(ES)+ m/e 474.4 [M+H]+.

Example 8

(S)-4-(4-(3-chloroquinolin-7-yl)-2-fluorophenyl)-1-methyl-3-((1-propionylpyrrolidin-3-yl)methyl)-1H-1,2,4-triazol-5(4H)-one

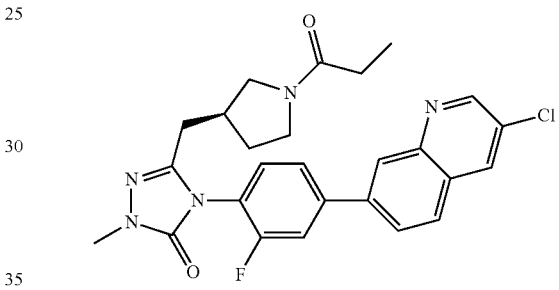

a) 3-chloro-7-(4,4,5,5-tetramethyl-1,3,2-dioxaborolan-2-yl)quinoline

To a 5 mL microwaveable vial were added 7-bromo-3-chloroquinoline (100 mg, 0.412 mmol), bis(pinacolato)diboron (110 mg, 0.433 mmol), potassium acetate (160 mg, 1.63 mmol), tetrakis(triphenylphosphine)palladium(0) (40 mg, 0.035 mmol), and 1,4-dioxane (2 mL). The vial was capped, purged with nitrogen, and stirred at 100° C. After 4 hours, the reaction mixture was cooled to room temperature and diluted with dichloromethane (10 mL). The solution was filtered through a plug of celite and sodium sulfate, and the plug was washed with dichloromethane (20 mL). The filtrate was concentrated in vacuo and the residue was dissolved in dichloromethane and washed with water (1×). The organic layer was separated, dried over sodium sulfate, filtered, and concentrated in vacuo. Purification of the residue by silica gel chromatography (0-10% methanol:dichloromethane) afforded the title compound (120 mg, 89%). MS(ES)+ m/e 289.8 [M+H]+.

b) (S)-4-(4-(3-chloroquinolin-7-yl)-2-fluorophenyl)-3-((1-propionylpyrrolidin-3-yl)methyl)-1H-1,2,4-triazol-5(4H)-one To a 5 mL microwaveable vial were added (S)-4-(4-bromo-2-fluorophenyl)-3-((1-propionylpyrrolidin-3-yl)methyl)-1H-1,2,4-triazol-5(4H)-one (165 mg, 0.414 mmol), 3-chloro-7-(4,4,5,5-tetramethyl-1,3,2-dioxaborolan-2-yl)quinoline (107 mg, 0.370 mmol), 1,4-dioxane (2 mL), and 2M aq potassium carbonate (1.000 mL). The vial was capped, purged with nitrogen, and stirred at 100° C. After 2 hours, the vial was allowed to cool to allow the phases to separate. The dioxane layer was decanted with a pipette and diluted with dichloromethane (10 mL). This organic layer was filtered through a plug of celite and sodium sulfate. The plug was washed with dichloromethane (30 mL) and the filtrate was concentrated in vacuo. Purification of the residue by silica gel chromatography (0-10% methanol:ethyl acetate) afforded the title compound (95 mg, 46%). MS(ES)+ m/e 480.2 [M+H]+.

c) (S)-4-(4-(3-chloroquinolin-7-yl)-2-fluorophenyl)-1-methyl-3-((1-propionylpyrrolidin-3-yl)methyl)-1H-1,2,4-triazol-5(4H)-one To a 10 mL round bottom flask containing (S)-4-(4-(3-chloroquinolin-7-yl)-2-fluorophenyl)-3-((1-propionylpyrrolidin-3-yl)methyl)-1H-1,2,4-triazol-5(4H)-one (117 mg, 0.244 mmol) was added potassium carbonate (100 mg, 0.724 mmol), N,N-dimethylformamide (DMF) (2 mL), and iodomethane (20 µL, 0.32 mmol). The reaction mixture was stirred at 80° C. for 16 h, at which point additional iodomethane (20 µL, 0.32 mmol) was added. After the reaction mixture was stirred at 80° C. for 16 h, analysis of an aliquot by LCMS indicated the reaction had progressed to >95% completion. The reaction mixture was cooled to room temperature, diluted with dichloromethane (50 mL), and washed with brine (5×). The organic layer was collected, dried over sodium sulfate, filtered, and concentrated in vacuo. Purification of the residue by reverse phase HPLC (20-50% acetonitrile:water with 0.1% TFA) and neutralization of the recovered product by filtering a solution of it in acetonitrile (2 mL) through a macroporous solid phase extraction plug (PL-HCO3, 100 mg, 0.18 mmol) afforded the title product, after concentration in vacuo, as a white solid (61 mg, 46%). MS(ES)+ m/e 494.1 [M+H]+.

Example 9

(S)-4-(4-(3-chloroquinolin-7-yl)-2-fluorophenyl)-3-((1-(cyclopropanecarbonyl)pyrrolidin-3-yl)methyl)-1-methyl-1H-1,2,4-triazol-5(4H)-one

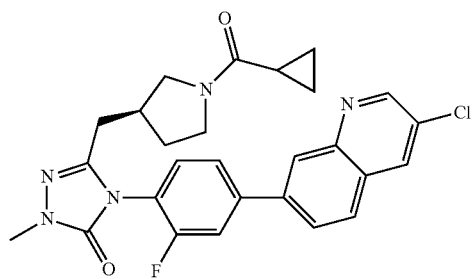 [SMILES: Cn1nc(C[C@@H]2CCN(C(=O)C3CC3)C2)n(-c2ccc(-c3ccc4cc(Cl)cnc4c3)cc2F)c1=O]

a) Following the procedure described in Example 8c with (S)-4-(4-(3-chloroquinolin-7-yl)-2-fluorophenyl)-3-((1-(cyclopropanecarbonyl)pyrrolidin-3-yl)methyl)-1-methyl-1H-1,2,4-triazol-5(4H)-one provided the title compound as a light brown solid (60 mg, 49%). MS(ES)+ m/e 506.0 [M+H]+.

Example 10

(S)-4-(2-fluoro-4-(3-fluoroquinolin-7-yl)phenyl)-1-methyl-3-((1-propionylpyrrolidin-3-yl)methyl)-1H-1,2,4-triazol-5(4H)-one

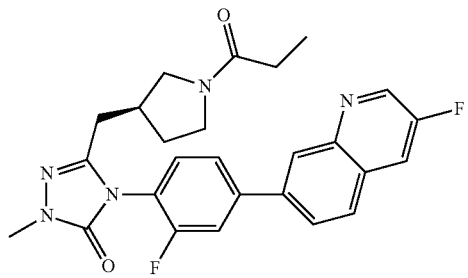 [SMILES: CCC(=O)N1CC[C@@H](Cc2nn(C)c(=O)n2-c2ccc(-c3ccc4cc(F)cnc4c3)cc2F)C1]

a) Following the procedure described in Example 8c with (S)-4-(2-fluoro-4-(3-fluoroquinolin-7-yl)phenyl)-3-((1-propionylpyrrolidin-3-yl)methyl)-1H-1,2,4-triazol-5(4H)-one provided the title compound as a light brown solid (45 mg, 34%). MS(ES)+ m/e 477.9 [M+H]+.

Biological Data

Exemplified compounds of the present invention (Examples 1-10) were tested according to at least one of the biological assays described herein and were found to be inhibitors of FAS.

FAS Assay

FAS activity was measured through one of the two following assays.

Assay #1:

Inhibition of FAS activity can be measured based on the detection of residual NADPH substrate after the FAS assay is quenched. This assay is run as a 10 µL endpoint assay in 384-well format, where the reaction contains 20 µM malonyl-CoA, 2 µM acetyl-CoA, 30 µM NADPH and 40 nM FAS in 50 mM sodium phosphate, pH 7.0. The assay is run by sequentially dispensing 5 µl of a malonyl-CoA solution, then enzyme solution (containing the acetyl-CoA, and NADPH) into a black, low volume assay plate (Greiner 784076) pre-dispensed with 100 nL compound solutions in DMSO. The reaction is incubated at ambient temperature for 60 minutes, then quenched with 5 µL of a developing solution composed of 90 µM resazurin, 0.3 IU/ml diaphorase in 50 mM sodium phosphate, pH 7.0. The developed reaction is read on a Molecular Devices Analyst or Acquest (or equivalent) plate reader using a 530 nm excitation wavelength filter, a 580 nm emission filter, and 561 nm dichroic filter. The test compounds are prepared in neat DMSO at a concentration of 10 mM. For inhibition curves, compounds are diluted using a three-fold serial dilution and tested at 11 concentrations (e.g. 25 µM-0.42 nM). Curves are analysed using ActivityBase and XLfit, and results are expressed as pIC50 values.

Assay #2:

Inhibition of FAS can also be quantified based on the detection of the CoA products with a thio-reactive coumarin dye. This assay is run as a 10 µL endpoint assay in 384-well format, where the reaction contains 20 µM malonyl-CoA, 20 µM acetyl-CoA, µM NADPH and 2 nM FAS in 50 mM sodium phosphate, pH 7.0, and 0.04% Tween-20. The assay is run by adding 5 µL enzyme solution to a black, low volume assay plate (Greiner 784076) pre-dispensed with 100 nl compound solutions in DMSO. After 30 minutes, 5

μL substrate is added, and the reaction incubated at ambient temperature for an additional 60 minutes. The reaction is then quenched with 10 μL of 6M guanidine-HCl containing 50 μM CPM (7-diethylamino-3-(4'-maleimidylphenyl)-4-methylcoumarin (CPM; thio-reactive dye), and incubated for 30 minutes. The plate is read on an Envision (PerkinElmer) or equivalent plate reader using a 380 nm excitation wavelength filter, and a 486 nm emission filter. Data fitting and compound preparations are done as described above.

Lipogenesis Assay

Cultured primary human pre-adipocytes (Zen-Bio, Cat#ASC062801) are plated at confluence (3×104 cells/well) in 96-well plates (Costar, Cat#3598) coated with 0.2% gelatin (Sigma, Cat#G-6650) in DMEM/F12 medium (InvitroGen Cat#11330-032) supplemented with 10% heat inactivated fetal bovine serum (InvitroGen, Cat#16000-044). The following day (day 1) the cell differentiation is induced by replacing the seeding medium with the differentiation medium composed of DMEM/F12 medium supplemented with 10% heat inactivated fetal bovine serum, 200 μM 3-isobutyl-1-methylxanthine (Sigma, Cat#I-5879), 20 nM dexamethasone (Sigma, Cat#D-8893), 20 nM GW1929 (Sigma, Cat#G5668) and 20 nM insulin (InvitroGen, Cat#03-0110SA). On day 7, differentiation medium is replaced by the re-feed medium made of DMEM/F12 supplemented with 10% heat inactivated serum and 20 nM insulin. The appropriate concentration of tested compounds and controls are added into this medium at that time. On day 12, the relative amount of cellular triglyceride is estimated by using a Trinder kit (Sigma, Cat#TR0100). Re-feed medium is aspirated and cells are washed with PBS (InvitroGen, Cat#14190-144) and the assay is performed according the kit manufacturer protocol. Briefly, reconstituted solutions A and B are mixed with 0.01% digitonin (Sigma, Cat#D-5628) prior to performing the assay and added onto the cells; plates are incubated at 37° C. for one hour. The absorbance is read at 540 nm. The data is first normalized using the following equation: 100*((UNK−Control 1)/(Control 2−Control 1)) where Control 1 is the Robust Mean of the 0% response control and Control 2 is the Robust Mean of the 100% response control. When multiple dilutions of compounds are tested, pXC50 are calculated from curves using the 4-parameter curve fitting with the following equation: y=(a−d)/(1+(s/c)^b)+d and with IRLS (Iterative Re-weighted Least Squares) algorithms to weight outliers (Mosteller, F. & Tukey J. W. (1977) Data Analysis and Regression, pp 353-365, Addison-Wesley).

DMPK Assays

Mouse and rat pharmacokinetic studies were performed generally as described in Xiang et al. (Preclinical drug metabolism and pharmacokinetic evaluation of GW844520, a novel mitochondrial electron transport inhibitor. H Xiang, J McSurdy-Freed, G Subbanagounder, E Hugger, R Bambal, C Han, S Ferrar, D Gargallo and CB Davis. (2006) *Journal of Pharmaceutical Sciences*, 95:2657-2672) and Davis et al. (Comparative preclinical drug metabolism and pharmacokinetic evaluation of novel 4-aminoquinoline anti-malarials. C B Davis, R Bambal, G S Moorthy, E Hugger, H Xiang, B Kevin Park, A E Shone, P M O'Neill and S A Ward (2009) *Journal of Pharmaceutical Sciences*, 98:362-377) with the following exceptions. For some mouse studies, cannulated animals were used and serial blood samples were collected from the individuals (n=2/compound/route of administration) as opposed to using a composite study design. In some iv rat studies, drugs were infused for 1 or 2 h and a single blood sample collected to estimate clearance assuming steady-state conditions (n=2/compound). This assay was employed as an initial PK screen to prioritize compounds for further study.

Biological and Pharmacokinetic Data

Exemplified compounds of the present invention were found to be potent inhibitors of human FAS. The $IC_{50}$ values versus human FAS were <20 nM, determined from at least one experiment or the average of multiple experiments for the compounds of the invention.

Rodent pharmacokinetic (PK) data were collected on the exemplified compounds according to the methods described above. These data are shown in Table 1. In vivo clearance (Cl) data are reported as the average of 1 to 4 animals across 1 to 2 experiments and are categorized as follows. In rats, a 'low' clearance is designated as <17 mL/min/kg, a 'moderate' clearance is designated as 17-39 mL/min/kg, and a 'high' clearance is designated as >39 mL/min/kg. In mice, a 'low' clearance is designated as <30 mL/min/kg, a 'moderate' clearance is designated as 30-70 mL/min/kg, and a 'high' clearance is designated as >70 mL/min/kg. In vivo oral exposure (po) data, reported as average dose-normalized AUCs (DNAUC) per experiment of 2-3 animals, are categorized as 'poor' for DNAUC ≤101 ng·h/mL/mg/kg and 'good' for DNAUC >101 ng·h/mL/mg/kg. When multiple experiments were performed under different conditions, the totality of the data was considered. In cases where both 'poor' and 'good' oral exposures were observed, a designation of 'mixed' is utilized to represent mixed and unoptimized results.

For comparison purposes, the PK data for two representative and related triazolones from WO2011/103546A1, which is incorporated by reference herein in its entirety, Examples 124 and 196, are shown, the structures of which are shown below.

5-{[(3S)-1-(cyclopropylcarbonyl)-3-pyrrolidinyl]methyl}-4-[2-fluoro-4-(7-quinolinyl)phenyl]-2,4-dihydro-3H-1,2,4-triazol-3-one

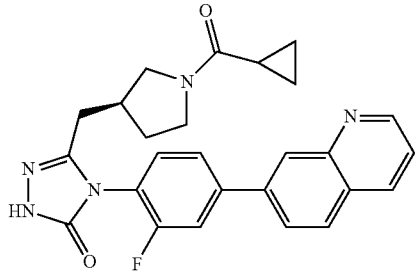 [SMILES: O=C(C1CC1)N1CC[C@@H](Cc2n[nH]c(=O)n2-c2ccc(-c3ccc4cccnc4c3)cc2F)C1]

Example 124 from WO2011/103546A1

4-[2-fluoro-4-(7-quinolinyl)phenyl]-5-{[(3S)-1-propanoyl-3-pyrrolidinyl]methyl}-2,4-dihydro-3H-1,2,4-triazol-3-one

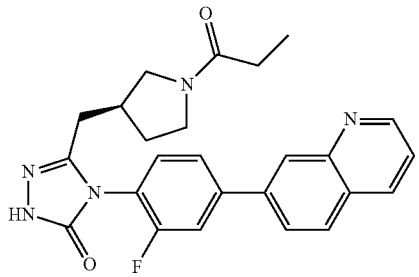 [SMILES: CCC(=O)N1CC[C@@H](Cc2n[nH]c(=O)n2-c2ccc(-c3ccc4cccnc4c3)cc2F)C1]

Example 196 from WO2011/103546A1

In the exemplified compounds herein, incorporation of a substituent at the 3-position of the quinoline led to noticeable improvements (reduced iv Cl, such as high to moderate or moderate to low, or improved oral exposure, such as poor to good or poor to mixed) in the rat and/or mouse PK profiles as compared to the parent reference examples. See Table 1 below.

TABLE 1

| Example No. | Rat iv Cl | Rat po DNAUC | Mouse iv Cl | Mouse po DNAUC |
|---|---|---|---|---|
| #124 from WO2011/103546A1 | high | poor | moderate | poor |
| 1 | moderate | poor | low | good |
| 2 | moderate | good | low | good |
| 3 | moderate | not tested | not tested | not tested |
| 9 | moderate | good | low | not tested |
| #196 from WO2011/103546A1 | moderate | poor | moderate | poor |
| 4 | low | poor | low | good |
| 5 | low | good | low | mixed |
| 6 | moderate | good | low | mixed |
| 7 | low | good | low | good |
| 8 | low | good | low | good |
| 10 | low | not tested | low | not tested |

I claim:
1. A compound selected from the group consisting of:
(S)-4-(2-fluoro-4-(3-methylquinolin-7-yl)phenyl)-1-methyl-3-((1-propionylpyrrolidin-3-yl)methyl)-1H-1,2,4-triazol-5(4H)-one;
(S)-4-(4-(3-chloroquinolin-7-yl)-2-fluorophenyl)-1-methyl-3-((1-propionylpyrrolidin-3-yl)methyl)-1H-1,2,4-triazol-5(4H)-one; and
(S)-4-(2-fluoro-4-(3-fluoroquinolin-7-yl)phenyl)-1-methyl-3-((1-propionylpyrrolidin-3-yl)methyl)-1H-1,2,4-triazol-5(4H)-one;
or a pharmaceutically acceptable salt thereof.

2. The compound of claim 1 which is (S)-4-(2-fluoro-4-(3-methylquinolin-7-yl)phenyl)-1-methyl-3-((1-propionylpyrrolidin-3-yl)methyl)-1H-1,2,4-triazol-5(4H)-one, having the structure:

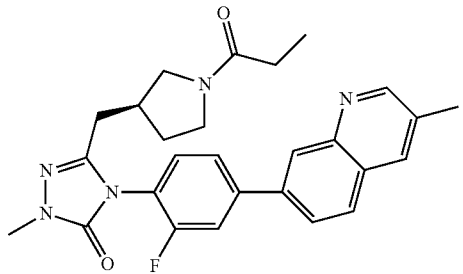

or a pharmaceutically acceptable salt thereof.

3. The compound of claim 1 which is (S)-4-(4-(3-chloroquinolin-7-yl)-2-fluorophenyl)-1-methyl-3-((1-propionylpyrrolidin-3-yl)methyl)-1H-1,2,4-triazol-5(4H)-one having the structure:

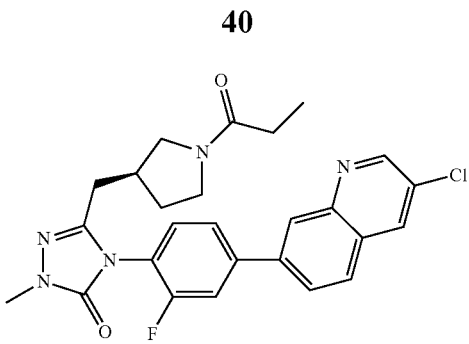

or a pharmaceutically acceptable salt thereof.

4. The compound of claim 1 which is (S)-4-(2-fluoro-4-(3-fluoroquinolin-7-yl)phenyl)-1-methyl-3-((1-propionylpyrrolidin-3-yl)methyl)-1H-1,2,4-triazol-5(4H)-one having the structure:

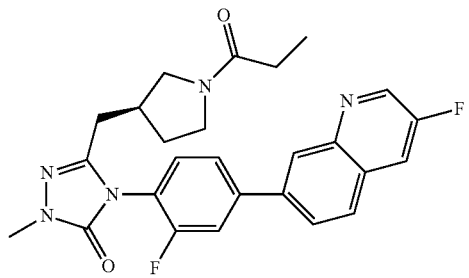 [SMILES: CCC(=O)N1CC[C@@H](Cc2nn(C)c(=O)n2-c2ccc(-c3ccc4cc(F)cnc4c3)cc2F)C1]

or a pharmaceutically acceptable salt thereof.

5. A pharmaceutical composition comprising a compound or pharmaceutically acceptable salt thereof according to any one of claims 1 to 4.

6. A method of treating cancer in a human in need thereof comprising administering to said human a compound or a pharmaceutically acceptable salt thereof according to any one of claims 1 to 4.

7. A method of treating cancer in a human in need thereof comprising administering to said human a pharmaceutical composition according to claim 5.

8. The method of claim 6 or 7 wherein the cancer is selected from the group consisting of: gastric, brain (gliomas), glioblastomas, leukemias, lymphomas, breast, inflammatory breast cancer, Wilm's tumor, Ewing's sarcoma, Rhabdomyosarcoma, ependymoma, medulloblastoma, colon, head and neck, kidney, lung, liver, melanoma, renal, ovarian, pancreatic, prostate, sarcoma, osteosarcoma, bladder, stomach, and giant cell tumor of bone and thyroid.

9. A method of treating cancer in a mammal in need thereof, which comprises: administering to such mammal a therapeutically effective amount of
a) a compound or a pharmaceutically acceptable salt thereof of claim 1; and
b) at least one anti-neoplastic agent.

10. A method of treating cancer in a human in need thereof comprising administering a compound or pharmaceutically acceptable salt thereof of claim 1 orally to said human at a dose of about 0.001 to about 100 mg/kg/day.

* * * * *